United States Patent [19]

Wanner et al.

[11] 4,042,235
[45] Aug. 16, 1977

[54] METHOD OF AN APPARATUS FOR UNSTACKING A PILE OF SHEETS

[75] Inventors: Rudolf Wanner, Aystetten; Robert Eckl, Augsburg, both of Germany

[73] Assignee: Fa. Böwe, Böhler & Weber KG Maschinenfabrik, Augsburg, Germany

[21] Appl. No.: 606,206

[22] Filed: Aug. 20, 1975

[30] Foreign Application Priority Data

Aug. 21, 1974 Germany .......................... 2440104

[51] Int. Cl.² .......................... B65H 3/08; B65H 3/10
[52] U.S. Cl. .......................... 271/94; 271/18; 271/30 A; 271/100; 271/105; 271/107; 271/112
[58] Field of Search .......................... 271/90, 94, 93, 96, 271/100, 102, 106, 107, 30 A, 150, 112, 118, 33, 99, 18 R

[56] References Cited

U.S. PATENT DOCUMENTS

| 3,073,460 | 1/1963 | Richert et al. | 271/150 X |
| 3,086,771 | 4/1963 | Goin et al. | 271/94 X |
| 3,166,311 | 1/1965 | Rabinow et al. | 271/96 X |
| 3,847,382 | 11/1974 | McKee | 271/118 X |

Primary Examiner—Bruce H. Stoner, Jr.
Attorney, Agent, or Firm—Karl F. Ross; Herbert Dubno

[57] ABSTRACT

A pile of sheets arranged vertically next to one another is gently urged against a rigid metal plate that can be reciprocated back and forth very rapidly so as to pull the end sheet off the pile by suction and to return to rest against the pile of sheets before they have followed this reciprocation motion to the same extent as the end sheet. Once the plate pulls rapidly away from the end of the pile, pulling the end sheet with it, this end sheet is engaged by a suction roller and pulled laterally off the pile.

10 Claims, 4 Drawing Figures

METHOD OF AN APPARATUS FOR UNSTACKING A PILE OF SHEETS

FIELD OF THE INVENTION

The present invention relates to a method of and an apparatus for unstacking a pile of sheets. More particularly this invention concerns a device for taking sheets, envelopes, leaves and the like from one end of a stack and feeding them out one-by-one.

BACKGROUND OF THE INVENTION

In the commonest prior-art system a stack of sheets, envelopes, or the like is pressed against a so-called suction roller. The roller is rotated in steps and the suction is applied with each step-wise advance.

The principal difficulty with this arrangement is that the roller very frequently picks up more than one sheet. This is due to the fact that the sheets tend to cling together and that the force with which the stack is pressed against the suction roller is excessive. This force also varies as the stack decreases in size.

OBJECTS OF THE INVENTION

It is therefore an object of the present invention to provide an improved method of and apparatus for unstacking a pile or pack of sheets.

Another object is the provision of such a method which carefully removes only the end element from a pile of sheets, envelopes, or the like.

SUMMARY OF THE INVENTION

These objects are attained according to the present invention in an unstacking method wherein the pile is urged continuously against a flat rigid plate so that an end sheet of the pile presses toward a plate. This plate is pulled away from the end sheet of the pile with a speed sufficient to lift the end sheet from the other sheets of the pile by suction and thus separate the end sheet from the next following sheet. Thereafter this end sheet is withdrawn laterally parallel to the plate from the pile and the plate is displaced back against the pile before this pile has had time to move significantly toward the plate so that the next sheet of the pile becomes the end sheet. Thereupon the plate is again pulled rapidly away from the subsequently uncovered end sheet to unstack the pile sheet-by-sheet. Thus this plate against which the stack is urged is oscillated or reciprocated back and forth very rapidly, separating the end sheet from the stack.

According to other features of this invention the plate is pivotal about an axis lying substantially at the end of the stack and is formed with at least one cutout aligned with a suction roller so that when the plate is withdrawn from the stack, pulling the end sheet with it, this end sheet is engaged by the suction roller which then laterally withdraws only this end sheet.

In accordance with yet another feature of this invention the pile is comprised of a plurality of upright sheets which are urged horizontally against the plate. With this type of system, rather than with the well-known gravity-feed arrangement, the force with which the stack is urged against the plate remains constant even when only a few sheets are left in the stack. Indeed it is possible with this arrangement to feed accurately down to the very last sheet of the stack.

The system according to the present invention relies on the suction created between the flat plate and the end sheet. This suction or adhesion is effective perpendicular to the plane of the sheet so as to separate it from the next sheet of the stack or pile. Friction between the end sheet and the adjoining sheet therefore becomes an almost irrelevant factor in the separation of the sheets from each other, since the end sheet does not slide off the next sheet.

According to another feature of this invention the plate is oscillated back and forth by a crank mechanism. Furthermore a valve connected to the suction roller is operated only when the plate is withdrawn so as to insure proper gripping and lateral withdrawal of the end sheet.

The means for urging the stack against the plate according to this invention comprises a plate parallel to the displaceable plate and a plurality of belts on which this second plate and the stack rest. The belts are driven continuously at very low speed so as gently to urge the entire stack and the support plate against the pivotal plate. A slip coupling may be provided to drive these belts so as to ensure constant pressing force.

BRIEF DESCRIPTION OF THE DRAWING

The above and other objects, features, and advantages will become more readily apparent from the following description, reference being made to the accompanying drawing in which.

SPECIFIC DESCRIPTION

Figure 3:
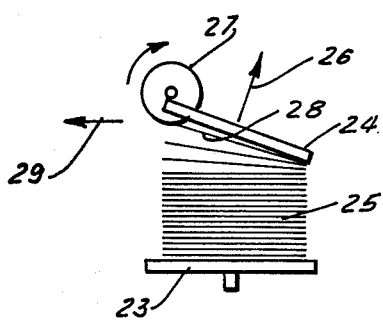
FIG. 3 is a schematic view illustrating the principles of operation of the apparatus in accordance with this invention.

As illustrated in FIG. 3 the apparatus according to the present invention has a plate 24 against which a stack of sheets 25 is urged by a support plate 23. The plate 24 is displaceable very rapidly in the direction indicated by arrow 26 so as to lift by suction the end sheet 28 from the stack 25. The plate 24 is withdrawn in the direction 26 such that the end sheet 28 comes to lie against a suction roller 27 which rotates in a direction serving to laterally withdraw the sheet 28 in the direction of arrow 29. The plate 24 is displaced with such rapidity that it lifts the end sheet 28 by suction, leaving the other sheets in the pile less disturbed.

Figure 1:
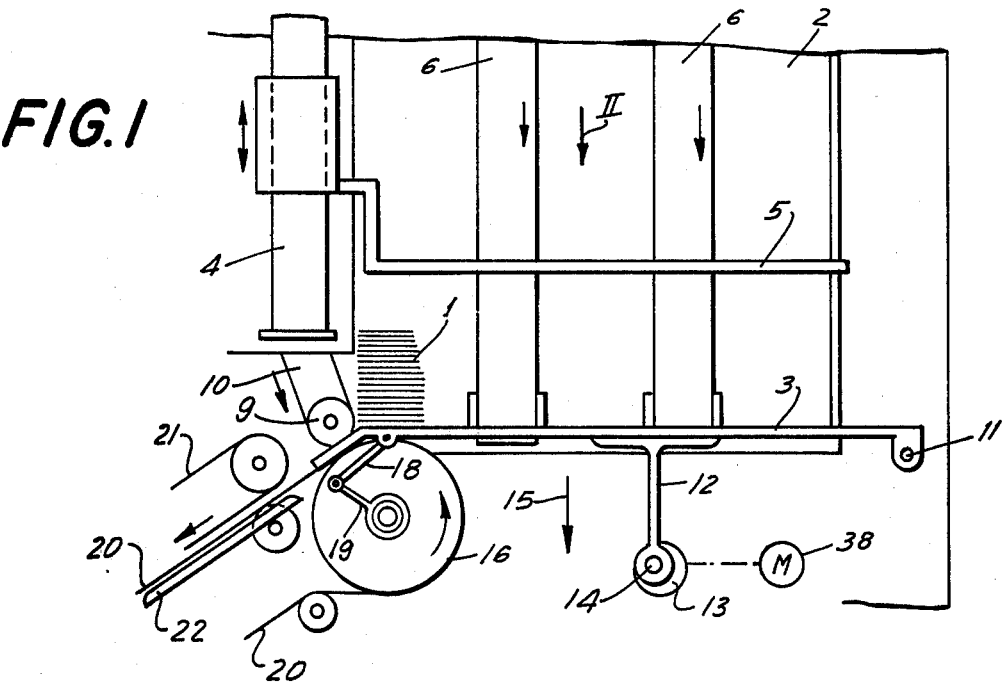
FIG. 1 is a top view of an apparatus for carrying out the method according to this invention.
Figure 2:
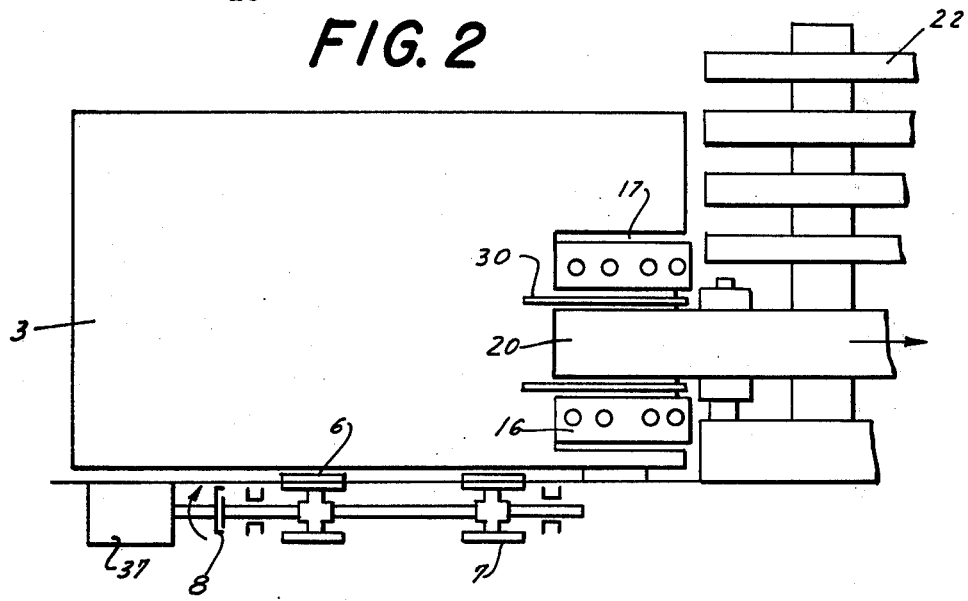
FIG. 2 is a side view taken in the direction of arrow II of FIG. 1.

This is carried out as illustrated in FIGS. 1 and 2 by an apparatus having a housing 2 on which a plate 3 is pivoted about a vertical axis 11. A stack of sheets 1 is pressed by an adjustment plate 5 slidable along a guide rod 4 against the plate 3 and is supported on a pair of belts 6 mounted on rollers 7 driven by a motor 37 through a slip clutch 8. These belts 6 also engage the support plate 5 so as to move it toward the plate 3. Thus the stack of sheets 1 is pressed with a constant force toward the plate 3, regardless of the type of sheets or thickness of stack. Indeed the pressure is the same whether fine sheets of onionskin-type paper form the stack, or manila envelopes.

The plate 3 is reciprocated back and forth by a motor 38 having an output shaft 13 on which is mounted an eccentric crank 14 connected via a flexible syntheticresin link 12 to the plate 3. The motor 38 is of the fast-acting servo type which can oscillate very rapidly from the position indicated in FIG. 1 in a counterclockwise direction through approximately 90° and back so as rapidly to displace the plate 3 from the illustrated position parallel to the support plate 15 in the direction of arrow 15 and back into this position.

A pair of vertically spaced suction rollers 16 flank a horizontally extending feed belt 20 and are aligned with a cutout 17 formed in the plate 3. Ribs 30 are provided on the side of the plate 3 toward the support plate 5 and serve to hold the sheets 1 out of contact with the rollers 16 when the plate 3 is in the position illustrated in FIG. 1.

Figure 4:
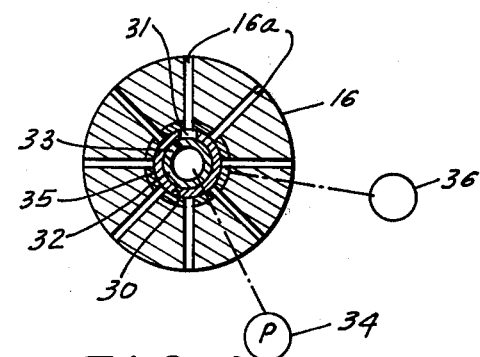
FIG. 4 is a section taken through one of the suction rollers according to the present invention.

Each of the rollers 16 as illustrated in FIG. 4 is formed with a plurality of angularly equispaced radially extending bores 16a that extend through a roller core sleeve 35 that is continuously rotated in a counterclockwise direction by a motor 36 that also serves to drive the belt 20. The core sleeve 35 is rotatable on a tube 30 formed with a longitudinally extending slot alignable with a similar such slot 33 in a central nonrotatable tube 32. The tube 30 is provided with an arm 19 connected via link 18 to the plate 3 so that deflection of this plate back in the direction of arrow 15 aligns the slots 31 and 33 and connects the suction hole 16a turned toward the stack to the interior of tube 32 and therefore to a suction pump 34. Thus, as the plate 3 is pulled back by the crank 14 the valve formed by the two tubes 30 and 32 is opened and draws in air through the hole 16a turned toward the stack 1.

Parallel to the belt 20 is another belt 21 snugly engaging the belt 20. A pair of guides 22 flank the arrangement and immediately opposite the rollers 16 is a belt 10 spaced slightly from the roller 16 and driven in the opposite direction so as to push any second sheet accidently engaged by the roller 16 back into the stack.

The device functions as follows.

The stack of sheets 1 is continuously urged with a relatively gentle pressure against the plate 3. The motor 38 rapidly reciprocates this plate 3 away from the stack, pulling away an end sheet that comes into engagement with the surface of the rollers 16. Simultaneously suction is applied to those holes 16a on the surface of the rollers 16 turned toward the stack so that this end sheet is adhered thereto and is drawn laterally off by the rotating rollers 16. Once it is pulled laterally somewhat out of the stack the sheet is gripped between the belts 21 and 20 and pulled completely away.

The reciprocation action is so very fast that only the end sheet is materially pulled away from the stack. The other sheets remain sufficiently in position so that the plate 3, as it returns to its original position, acts upon another end sheet which can be pulled from it.

We claim:

1. A method of unstacking a pile of sheets comprising the steps of:
   a. urging said pile continuously toward a flat rigid unperforated plate covering substantially the entire surface of a sheet at an end of the pile so that said end sheet of the pile presses against said plate;
   b. pulling said plate away from said end sheet of said pile with a speed sufficient to separate said end sheet from the next sheet of said pile by an adhesion created only by the contact of said plate with said end sheet and the movement of said plate away from the pile, said speed being in excess of the speed at which said pile is urged toward said plate;
   c. thereafter withdrawing said end sheet laterally parallel to said plate from said pile;
   d. thereafter displacing said plate back against said pile whereby the next sheet of said pile becomes the end sheet; and
   e. repeating steps (b), (c), and (d) with the subsequently uncovered end sheets.

2. The method defined in claim 1 wherein said plate is pulled away from said pile and displaced back against said pile by pivoting said plate oscillatingly about an axis lying generally at the end sheet of said pile.

3. The method defined in claim 2 wherein said pile comprises a multiplicity of upright sheets, said pile being urged horizontally against said plate.

4. An apparatus for unstacking a pile of sheets, said apparatus comprising:
   means for supporting said pile of sheets such that said pile has an end sheet at one end thereof;
   a rigid flat unperforated metal plate covering substantially the entire surface of said end sheet;
   means for urging said pile toward said plate with said end sheet of said pile pressing against said plate;
   means for displacing said plate back and forth between a position wherein said plate rests against said pile and a position wherein said plate is spaced from said pile, said displacing means shifting said plate between said positions with a speed sufficiently great that all but the end sheet of said pile do not materially follow the displacement of said plate but the end sheet is pulled away from the next sheet of said pile by adhesion created only by the contact of said plate with said end sheet and the movement of said plate, said speed being in excess of the speed at which the pile is urged toward said plate; and
   means for withdrawing said end sheet laterally parallel to said plate from said pile when said plate is spaced from said pile.

5. The apparatus defined in claim 4 wherein said plate is upright.

6. The apparatus defined in claim 4, further comprising means for mounting said plate for pivotal movement about an axis parallel to said plate.

7. The apparatus defined in claim 6 wherein said displacing means includes a rotatable crank and a link connecting said crank to said plate at a location spaced from said axis.

8. The apparatus defined in claim 4 wherein said means for withdrawing is a roller adjacent said plate, and a drive for rotating said roller.

9. The apparatus defined in claim 8 wherein said roller is formed with a plurality of radially opening apertures and is provided with means for drawing in air through said apertures for suctionally engaging said end sheet.

10. The apparatus defined in claim 9 wherein said roller has a surface spaced just behind said plate when said plate is against said pile and said plate is formed with an opening aligned with said roller, said roller projecting through said opening in said position of said plate spaced from said pile.

* * * * *